United States Patent
Spohn et al.

(10) Patent No.: US 9,259,527 B2
(45) Date of Patent: Feb. 16, 2016

(54) FLUID DELIVERY SYSTEM WITH HIGH AND LOW PRESSURE HAND MANIFOLD

(71) Applicant: Bayer Medical Care Inc., Indianola, PA (US)

(72) Inventors: Michael A Spohn, Fenelton, PA (US); Michael James Swantner, Saxonburg, PA (US); Barry Lynn McDaniel, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 358 days.

(21) Appl. No.: 13/755,883

(22) Filed: Jan. 31, 2013

(65) Prior Publication Data

US 2014/0107480 A1   Apr. 17, 2014

Related U.S. Application Data

(60) Provisional application No. 61/714,872, filed on Oct. 17, 2012.

(51) Int. Cl.
*A61M 5/00* (2006.01)
*A61M 39/22* (2006.01)
*A61M 5/14* (2006.01)

(52) U.S. Cl.
CPC ............ *A61M 5/007* (2013.01); *A61M 5/1408* (2013.01); *A61M 39/223* (2013.01); *A61M 2039/229* (2013.01)

(58) Field of Classification Search
CPC ..... A61M 5/007; A61M 5/14; A61M 5/1407; A61M 5/1408; A61M 5/1409; A61M 5/168; A61M 5/16827; A61M 39/22; A61M 39/223; A61M 2039/229

USPC ........................................... 604/248; 600/432
See application file for complete search history.

(56) References Cited

U.S. PATENT DOCUMENTS 5,460,609 A   10/1995   O'Donnell
5,540,668 A *  7/1996   Wilson et al. ................. 604/248
(Continued)

FOREIGN PATENT DOCUMENTS

DE   202005015741 U1 *  1/2006
EP       1602388 B1 *  11/2009
(Continued)

OTHER PUBLICATIONS

Cheatham. Hemodynamic Monitoring: Principles to Practice. Surgical Crital Care Lecture. Jan. 13, 2009.
(Continued)

*Primary Examiner* — Theodore Stigell
*Assistant Examiner* — Amber Stiles
(74) *Attorney, Agent, or Firm* — Joseph L. Kent; David Schramm; James R. Stevenson

(57) ABSTRACT

A fluid delivery system is provided and includes a power injector supporting a high pressure syringe. The fluid delivery system further includes a manifold and a low pressure hand-operated syringe. The manifold generally includes a plurality of fluid control valves in series fluid communication. A first fluid control valve of the plurality of fluid control valves has a first port, a second inlet port, and a third port. The third port of the first fluid control valve is in fluid connection with a first port of a second fluid control valve. The low pressure hand-operated syringe is in fluid connection with the first port of the first fluid control valve, and the high pressure syringe is in fluid connection with the second port of the first fluid control valve. The fluid control valves may be multi-position stopcock valves.

22 Claims, 11 Drawing Sheets

(56) References Cited

U.S. PATENT DOCUMENTS

| | | | |
|---|---|---|---|
| 5,551,301 | A | 9/1996 | Cowan |
| 5,573,515 | A | 11/1996 | Wilson et al. |
| 5,631,552 | A | 5/1997 | Ogawa et al. |
| 5,800,397 | A | 9/1998 | Wilson et al. |
| 5,967,176 | A | 10/1999 | Blann et al. |
| 6,171,253 | B1 | 1/2001 | Bullister et al. |
| 6,650,929 | B1* | 11/2003 | Nemoto ............ A61M 5/007 600/431 |
| 7,094,216 | B2 | 8/2006 | Trombley, III et al. |
| 7,389,788 | B2 | 6/2008 | Wilson et al. |
| 7,556,619 | B2 | 7/2009 | Spohn et al. |
| 7,610,936 | B2 | 11/2009 | Spohn et al. |
| 7,713,239 | B2* | 5/2010 | Uber et al. .................... 604/131 |
| 8,147,464 | B2 | 4/2012 | Spohn et al. |
| 8,337,456 | B2 | 12/2012 | Schriver et al. |
| 8,361,040 | B2 | 1/2013 | Spohn et al. |
| 2004/0064041 | A1 | 4/2004 | Lazzaro et al. |
| 2004/0143225 | A1 | 7/2004 | Callan et al. |
| 2004/0221904 | A1* | 11/2004 | Usher et al. .................... 137/837 |
| 2005/0113754 | A1 | 5/2005 | Cowan |
| 2005/0234428 | A1* | 10/2005 | Spohn et al. .................. 604/533 |
| 2006/0009699 | A1 | 1/2006 | Roteliuk et al. |
| 2006/0079765 | A1* | 4/2006 | Neer et al. .................... 600/432 |
| 2006/0180202 | A1 | 8/2006 | Wilson et al. |
| 2008/0086087 | A1 | 4/2008 | Spohn et al. |
| 2008/0154214 | A1 | 6/2008 | Spohn et al. |
| 2009/0216192 | A1 | 8/2009 | Schriver et al. |
| 2012/0123257 | A1 | 5/2012 | Stokes, Jr. et al. |
| 2013/0197883 | A1 | 8/2013 | Grow et al. |
| 2014/0034169 | A1* | 2/2014 | Harton et al. ................. 137/798 |

FOREIGN PATENT DOCUMENTS

| | | |
|---|---|---|
| WO | 9422686 | 10/1994 |
| WO | 9522280 | 8/1995 |
| WO | 2012155035 | 11/2012 |

OTHER PUBLICATIONS

Omron. 7 Series Blook Pressure Monitor with ComFit Cuff. Instruction Manual. 2010.

The Notification of Transmittal of the ISR and the Written Opinion of the International Searching Authority in the corresponding PCT Application No. PCT/US2013/034896 filed on Apr. 2, 2013.

The International Search Report and Written Opinion of corresponding PCT Application No. PCT/US2013/064938.

The Non-Final Office Action dated Mar. 4, 2015 from related U.S. Appl. No. 13/798,709, filed Mar. 13, 2013.

The International Preliminary Report on Patentability from corresponding PCT Application No. PCT/US2013/064938.

* cited by examiner

FLUID DELIVERY SYSTEM WITH HIGH AND LOW PRESSURE HAND MANIFOLD

CROSS-REFERENCE TO RELATED APPLICATIONS

This application claims the benefit of U.S. Provisional Application No. 61/714,872, filed Oct. 17, 2012.

BACKGROUND OF THE INVENTION

1. Field of the Invention

This disclosure relates to medical fluid delivery applications and, particularly, a fluid delivery system comprising a fluid path set with a high and low pressure hand manifold for delivery of one or more medical fluids to a patient undergoing a medical diagnostic or therapeutic procedure.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media (often referred to simply as "contrast", have been developed for use in procedures such as angiography, computed tomography (CT), ultrasound, and NMR/MRI. In general, these powered injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort which provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Nonetheless, automatic contrast injection mechanisms provide improved control over manual apparatuses where successful use of such manual devices is dependent on the skill of the medical practitioner operating the device.

While manual and automated injectors are known in the medical field, improved fluid delivery systems adapted for use in medical diagnostic and therapeutic procedures where one or more fluids are supplied to a patient during the procedure continue to be in demand in the medical field. Additionally, improved fluid transfer sets and flow controlling and regulating devices associated therewith, which may be used with fluid delivery systems for conducting and regulating fluids flows, are also desired in the medical field. Moreover, the medical field continues to demand improved medical devices and systems used to supply fluids to patients during medical procedures such as angiography, computed tomography, ultrasound, and NMR/MRI.

SUMMARY OF THE INVENTION

In one embodiment, a fluid path set for a fluid delivery system is provided and comprises a manifold comprising a plurality of fluid control valves in series fluid communication. A first fluid control valve of the plurality of fluid control valves comprises a first port, a second port, and a third port. The third port of the first fluid control valve is in fluid connection with a first port of a second fluid control valve. A low pressure hand-operated syringe is in fluid connection with the first port of the first fluid control valve, and a high pressure syringe is in fluid connection with the second port of the first fluid control valve. The fluid control valves may comprise multi-position stopcock valves. The manifold may further comprise a manifold housing, and the fluid control valves may be in friction-fit connection within the manifold housing.

The manifold may further comprise an L-shaped manifold housing. The L-shaped manifold housing may comprise a longitudinal portion and a lateral portion, and the second port of the first fluid control valve may be generally coaxial with the lateral portion. The lateral portion may define a tubing retention pathway to accommodate tubing connecting the high pressure syringe with the second port of the first fluid control valve. The tubing retention pathway may define a tubing bend of approximately 90°. The manifold may further comprise a manifold housing, and the manifold housing may comprise a stop element to prevent rotation of the first fluid control valve to a position that opens a fluid path between the high pressure syringe and the low pressure syringe.

In another embodiment, a fluid delivery system is provided, comprising a power injector supporting a high pressure syringe. The fluid delivery system further comprises a manifold and a low pressure hand-operated syringe. The manifold generally comprises a plurality of fluid control valves in series fluid communication. A first fluid control valve of the plurality of fluid control valves comprises a first port, a second port, and a third port. The third port of the first fluid control valve is in fluid connection with a first port of a second fluid control valve. The low pressure hand-operated syringe is in fluid connection with the first port of the first fluid control valve, and the high pressure syringe is in fluid connection with the second port of the first fluid control valve. The fluid control valves may comprise multi-position stopcock valves.

The manifold may further comprise a manifold housing, and the fluid control valves may be in friction-fit connection within the manifold housing.

The manifold may further comprise an L-shaped manifold housing. The L-shaped manifold housing may comprise a longitudinal portion and a lateral portion, and the second port of the first fluid control valve may be generally coaxial with the lateral portion. The lateral portion may define a tubing retention pathway to accommodate tubing connecting the high pressure syringe with the second port of the first fluid control valve. The tubing retention pathway may define a tubing bend of approximately 90°. The manifold may further comprise a manifold housing, and the manifold housing may comprise a stop element to prevent rotation of the first fluid control valve to a position that opens a fluid path between the high pressure syringe and the low pressure syringe.

In a further embodiment, a fluid path set for a fluid delivery system is provided and comprises a manifold comprising a plurality of fluid control valves in series fluid communication, each of the fluid control valves comprising a first port, a second port, and a third outlet port. The third port of a first of the first fluid control valves is in fluid connection with the first port of a second of the fluid control valves, and the third port of the second fluid control valve is in fluid connection with the first port of a third of the fluid control valves. A low pressure hand-operated syringe is in fluid connection with the first port of the first fluid control valve, and a high pressure syringe is in fluid connection with the second port of the first fluid control valve. A hemodynamic pressure transducer may be in fluid connection with the second port of the third fluid control valve. The fluid control valves may comprise multi-position stopcock valves. The manifold may further comprise a manifold housing, and the fluid control valves may be in friction-fit connection within the manifold housing.

The manifold may further comprise an L-shaped manifold housing. The L-shaped manifold housing may comprise a longitudinal portion and a lateral portion, and the second port of the first fluid control valve may be generally coaxial with the lateral portion. The lateral portion may define a tubing retention pathway to accommodate tubing connecting the high pressure syringe with the second port of the first fluid control valve. The tubing retention pathway may define a tubing bend of approximately 90°. The manifold may further comprise a manifold housing, and the manifold housing may comprise a stop element to prevent rotation of the first fluid control valve to a position that opens a fluid path between the high pressure syringe and the low pressure syringe.

Further details and advantages of the various embodiments described in detail herein will become clear upon reviewing the following detailed description of the various embodiments in conjunction with the accompanying drawing figures.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Figure 1:
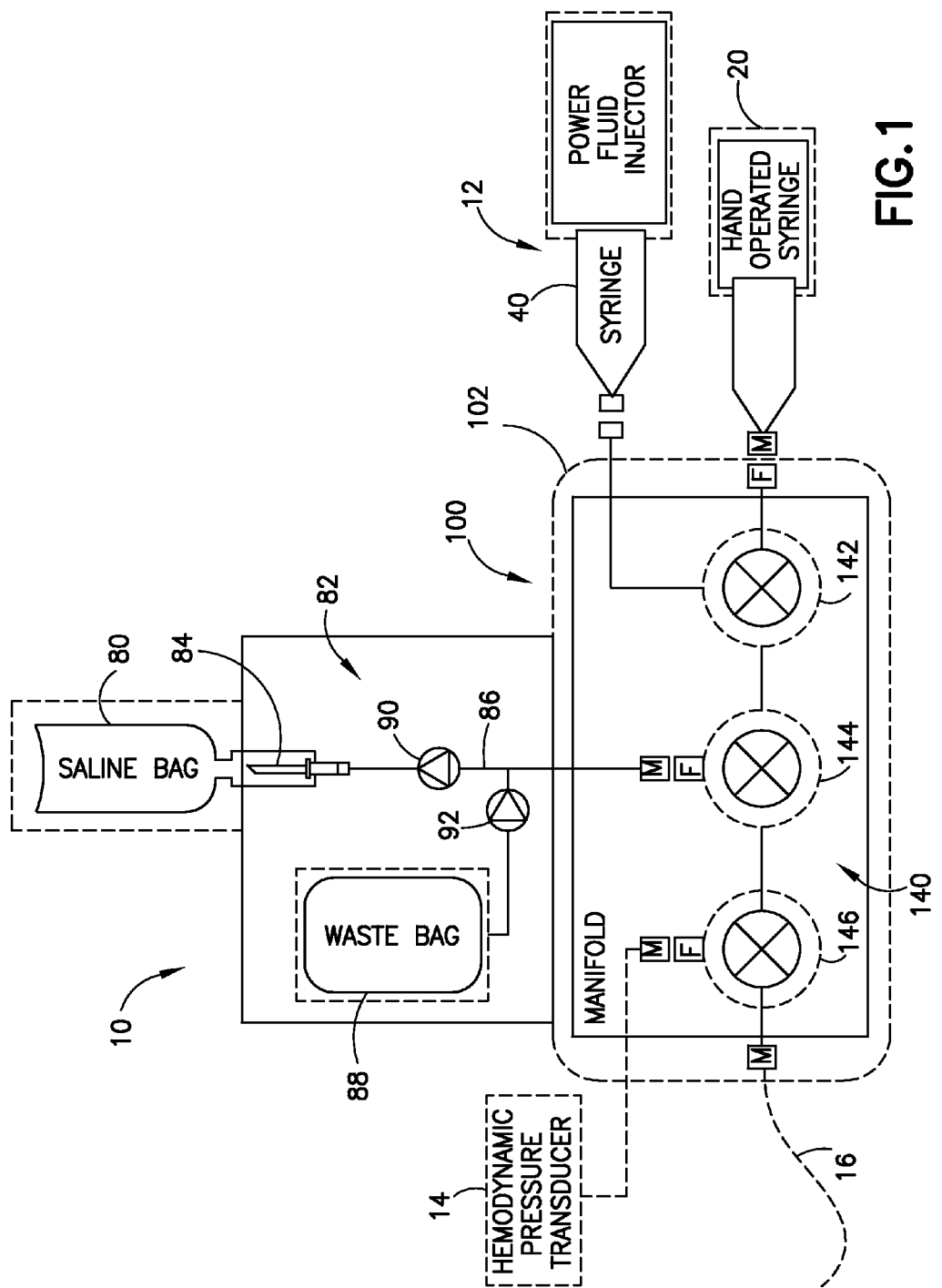
FIG. 1 is a schematic view of a fluid delivery system including a dual high and low pressure hand manifold.
Figure 2:
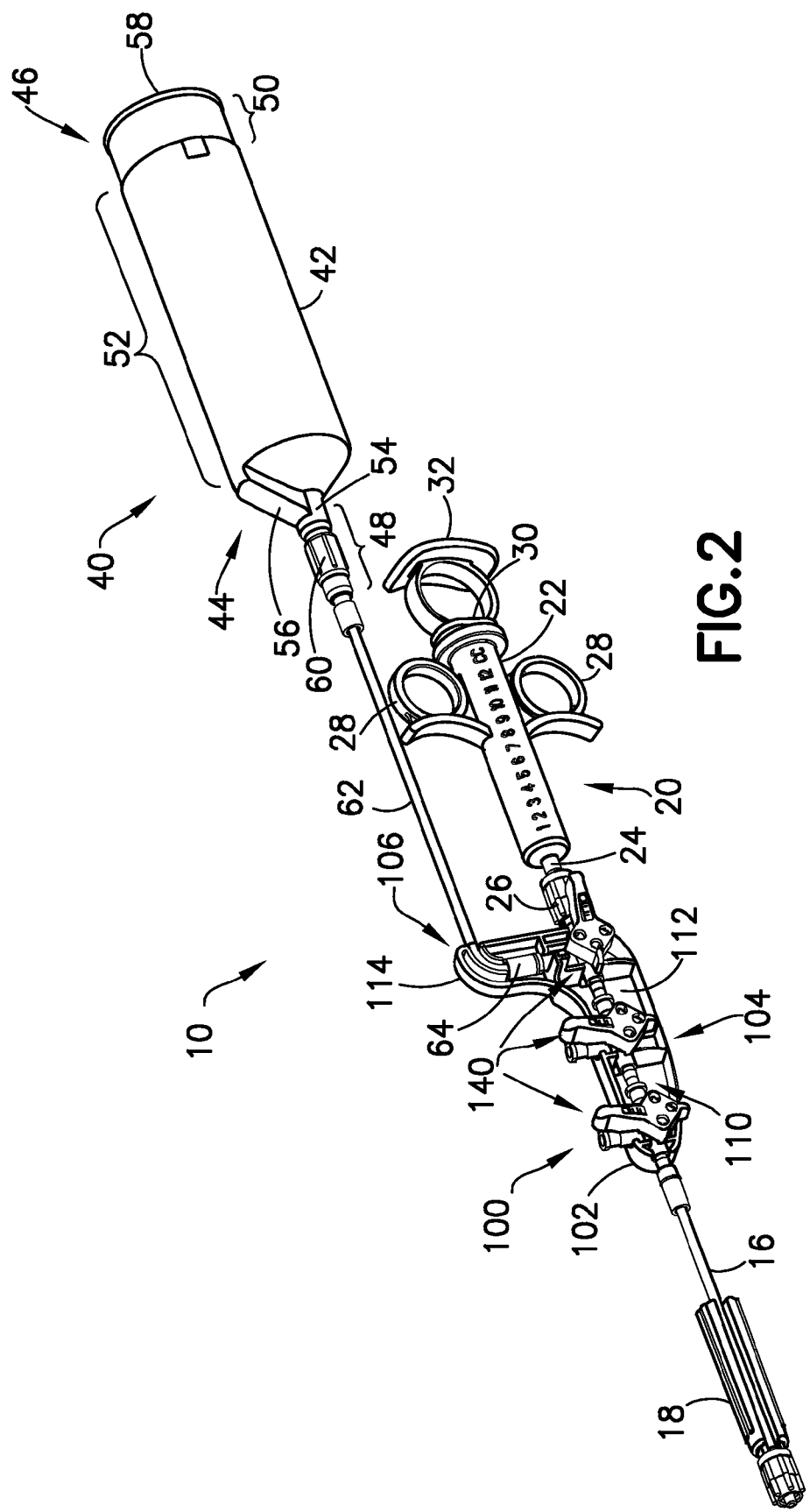
FIG. 2 is a perspective view of the fluid delivery system of FIG. 1 comprising a fluid path set incorporating the dual high and low pressure manifold.
Figure 3:
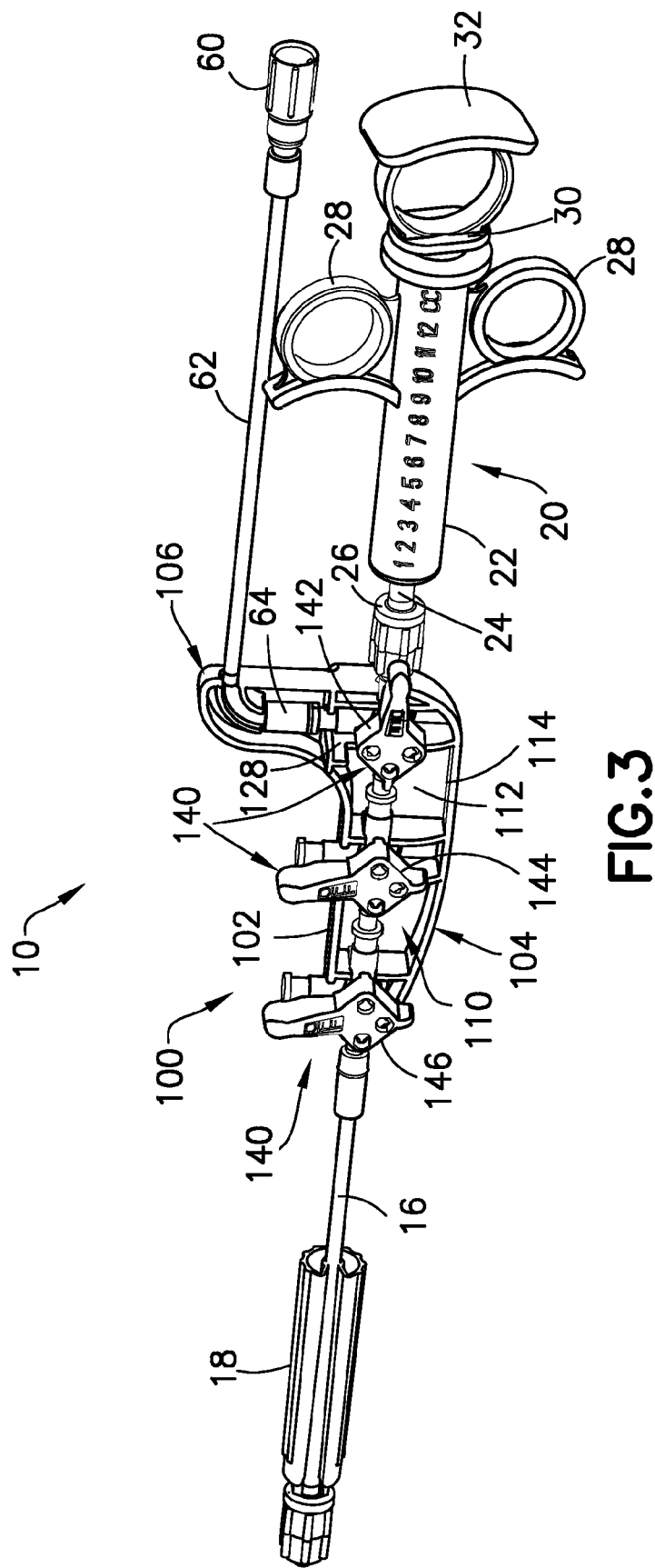
FIG. 3 is another perspective view of the fluid path set incorporating the dual high and low pressure manifold as shown in FIG. 2.
Figure 4:
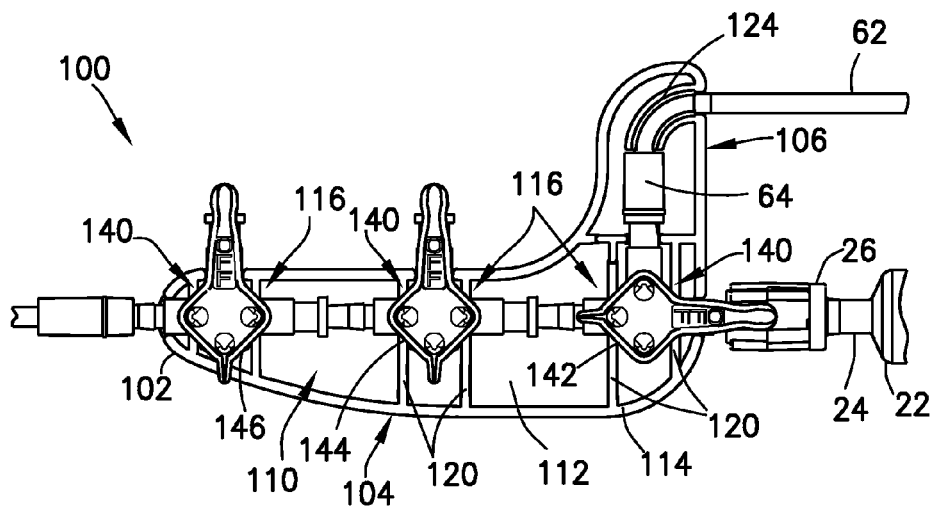
FIG. 4 is an elevational view of the manifold shown in FIGS. 2-3.
Figure 5:
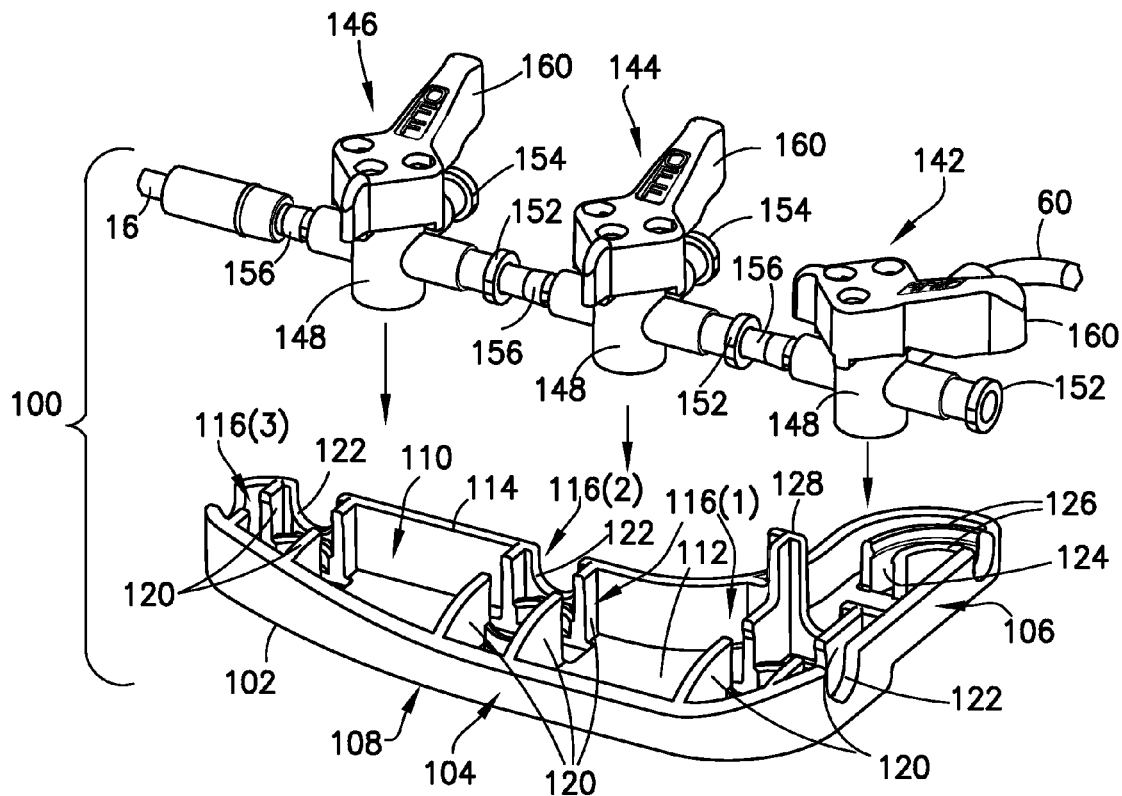
FIG. 5 is a perspective and exploded view of the manifold shown in FIG. 4.
Figure 6:
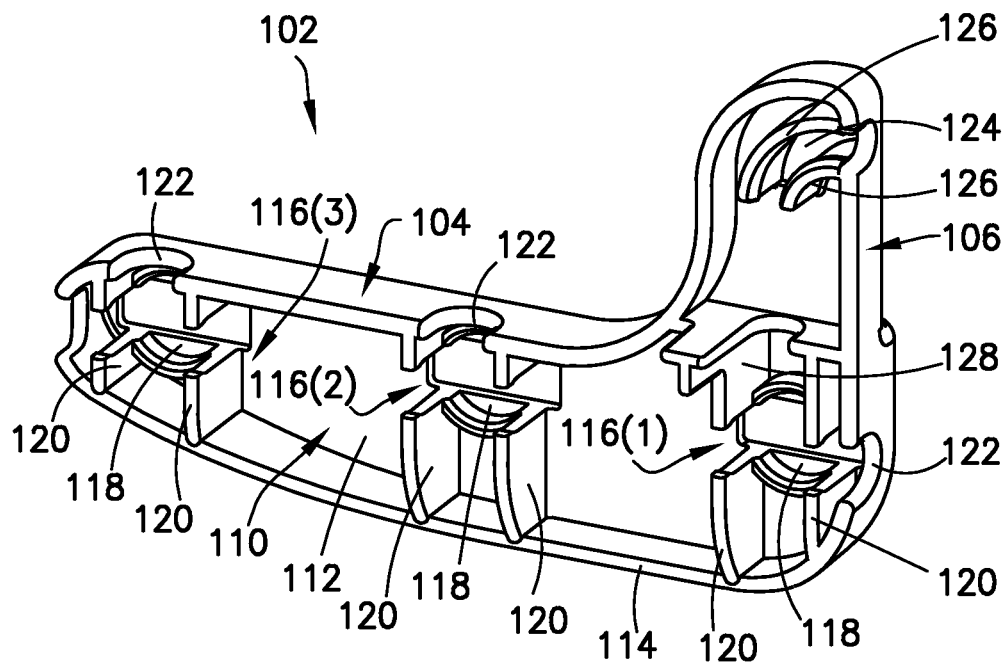
FIG. 6 is a perspective view of a manifold housing of the manifold shown in FIG. 4.
Figure 7:
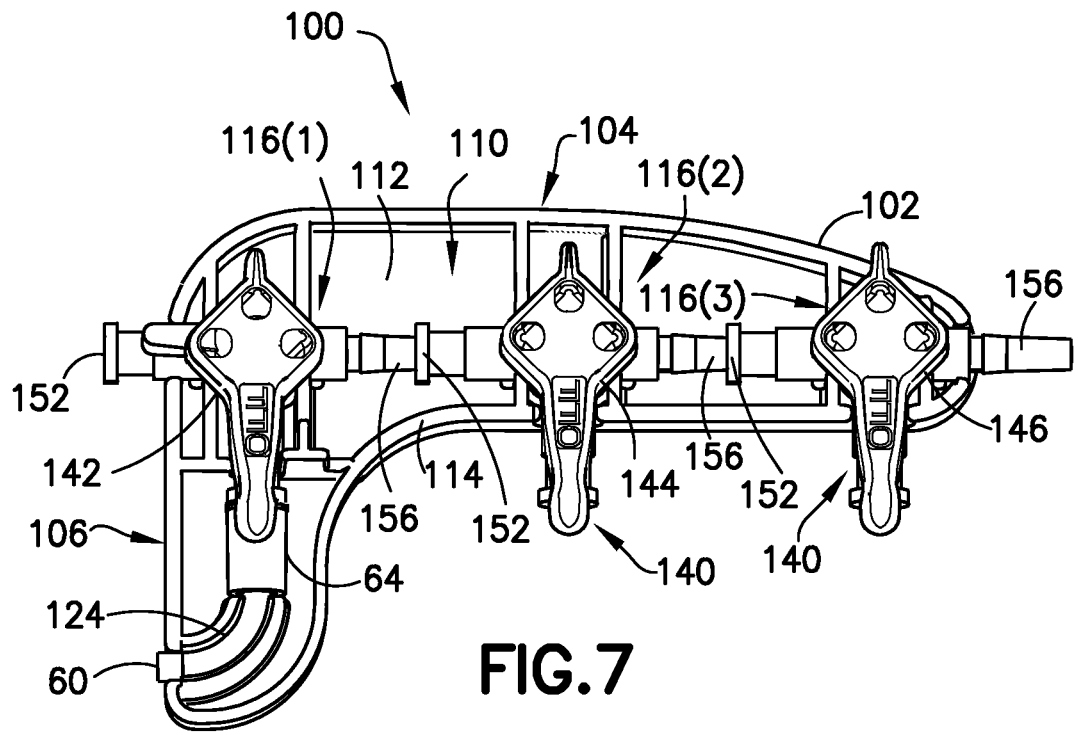
FIG. 7 is an elevational view showing a portion of the manifold shown in FIG. 4.
Figure 9A:
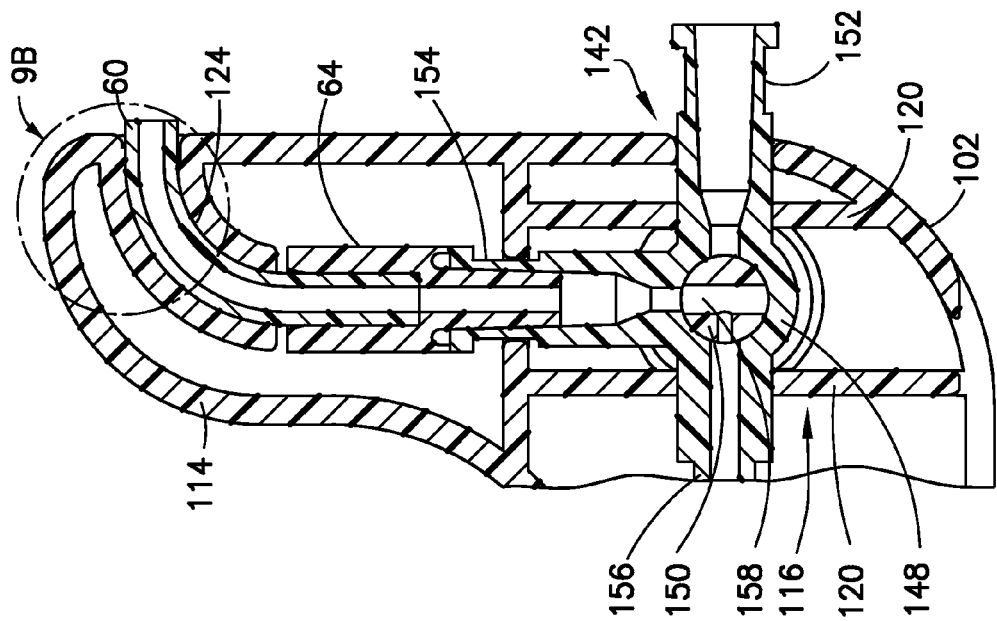
FIG. 9A is transverse cross-sectional view showing an end portion of the manifold shown in FIG. 7.
Figure 8:
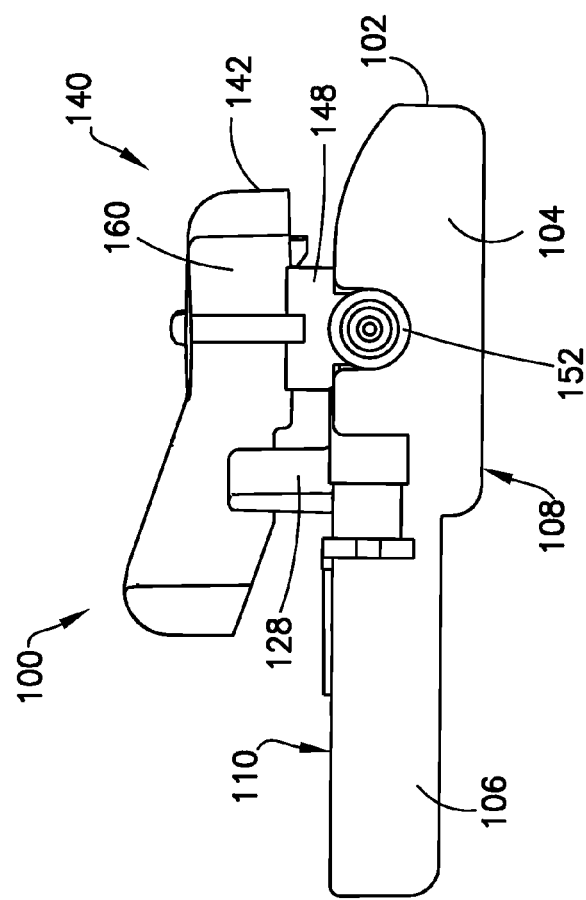
FIG. 8 is an end view of the manifold shown in FIG. 7.
Figure 9B:
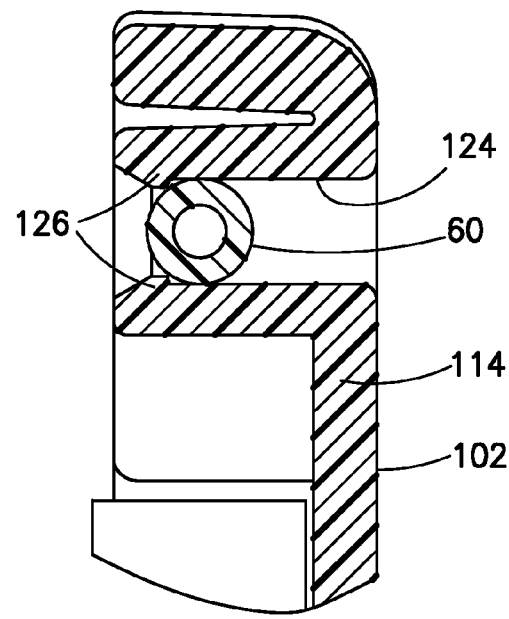
FIG. 9B is a detail view of Detail 9B in FIG. 9A.
Figure 12:
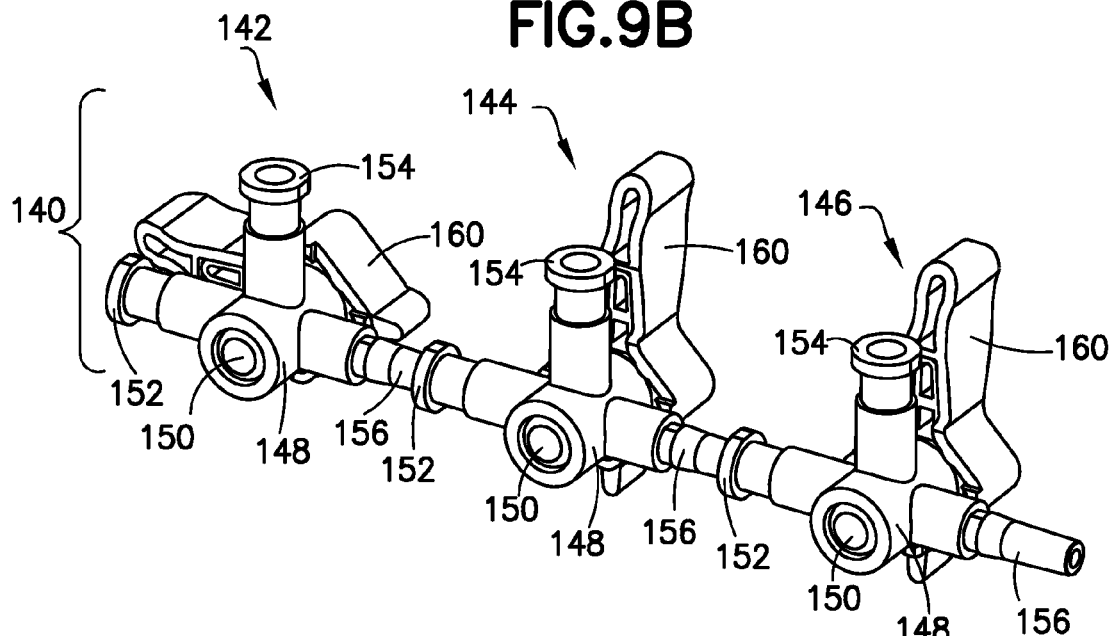
FIG. 12 is a perspective view showing fluid control valves connected in series as used in the manifold shown in FIG. 4.
Figure 10:
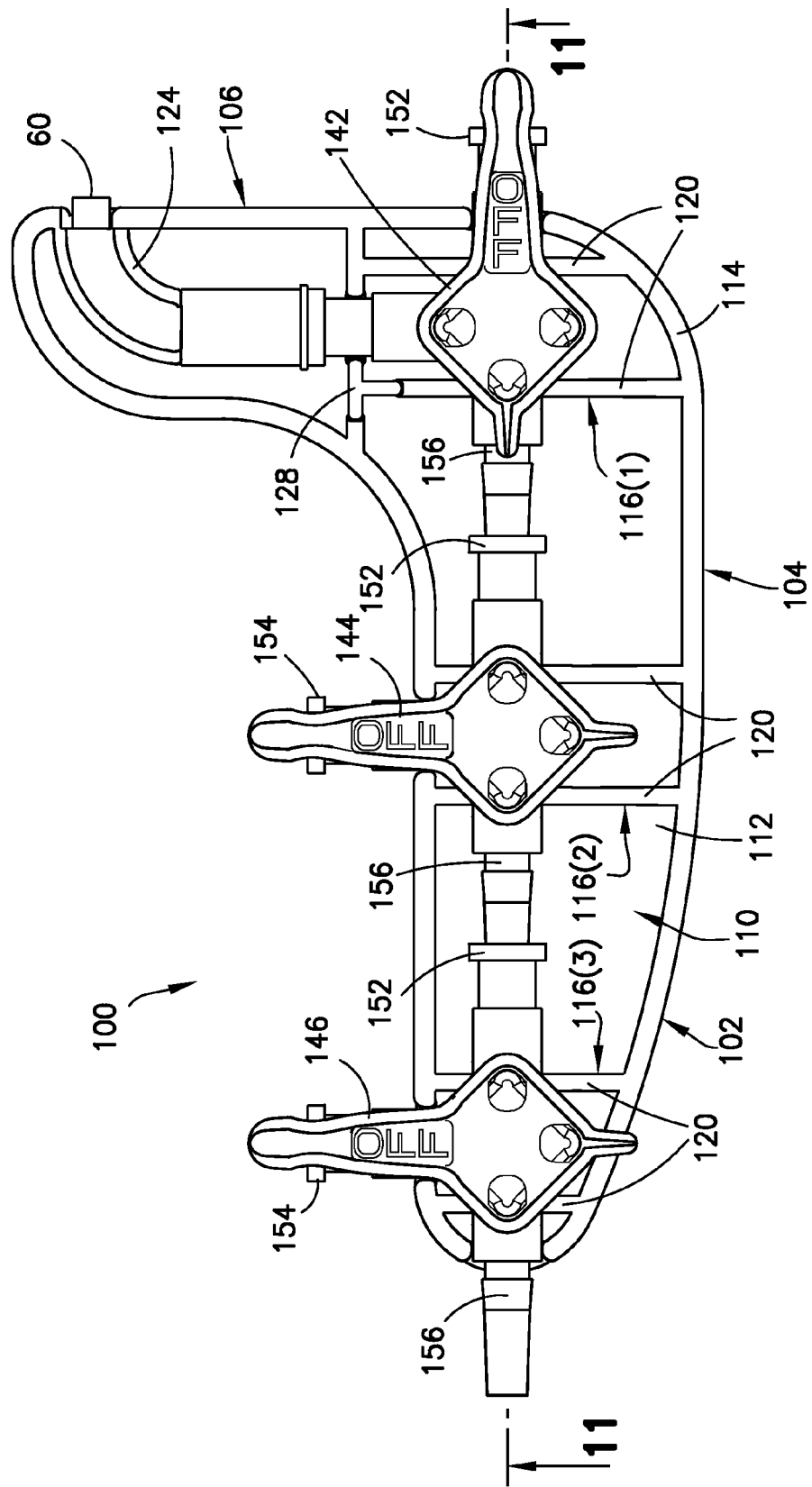
FIG. 10 is an elevational view of the manifold shown in FIG. 4.
Figure 11:
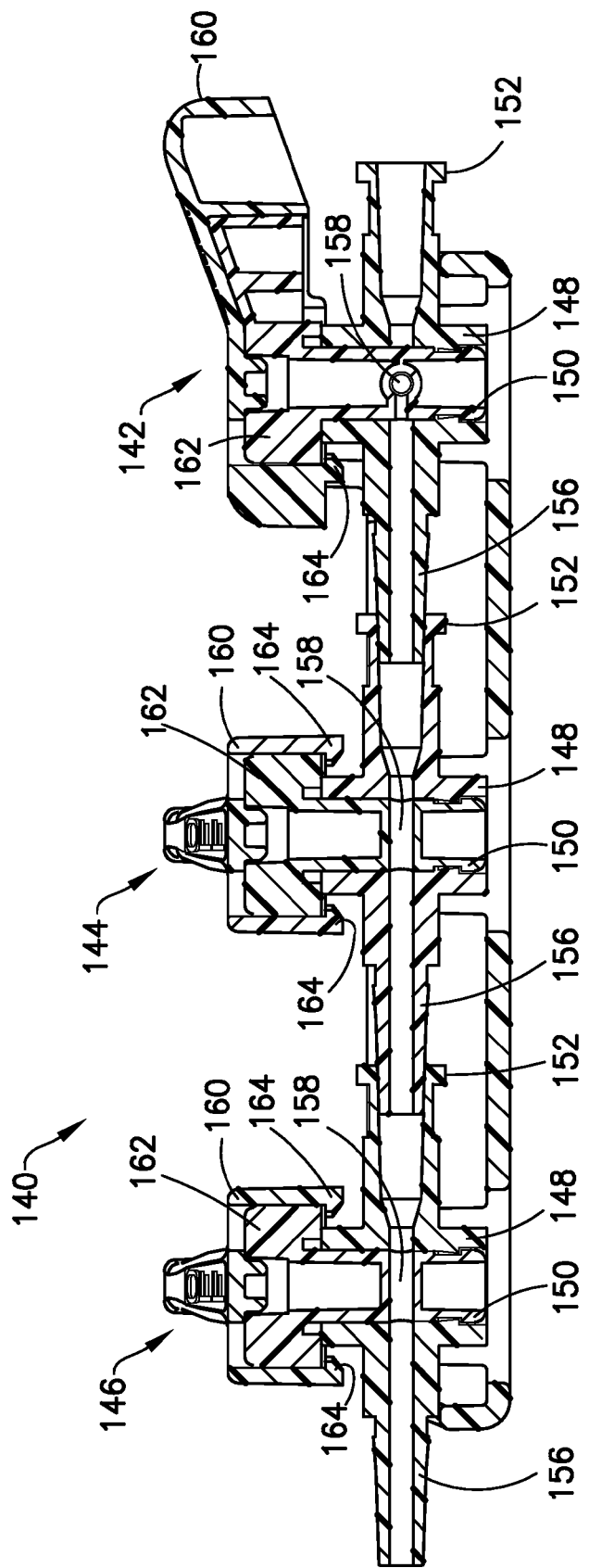
FIG. 11 is a cross-sectional view taken along lines 11-11 in FIG. 10.
Figure 13:
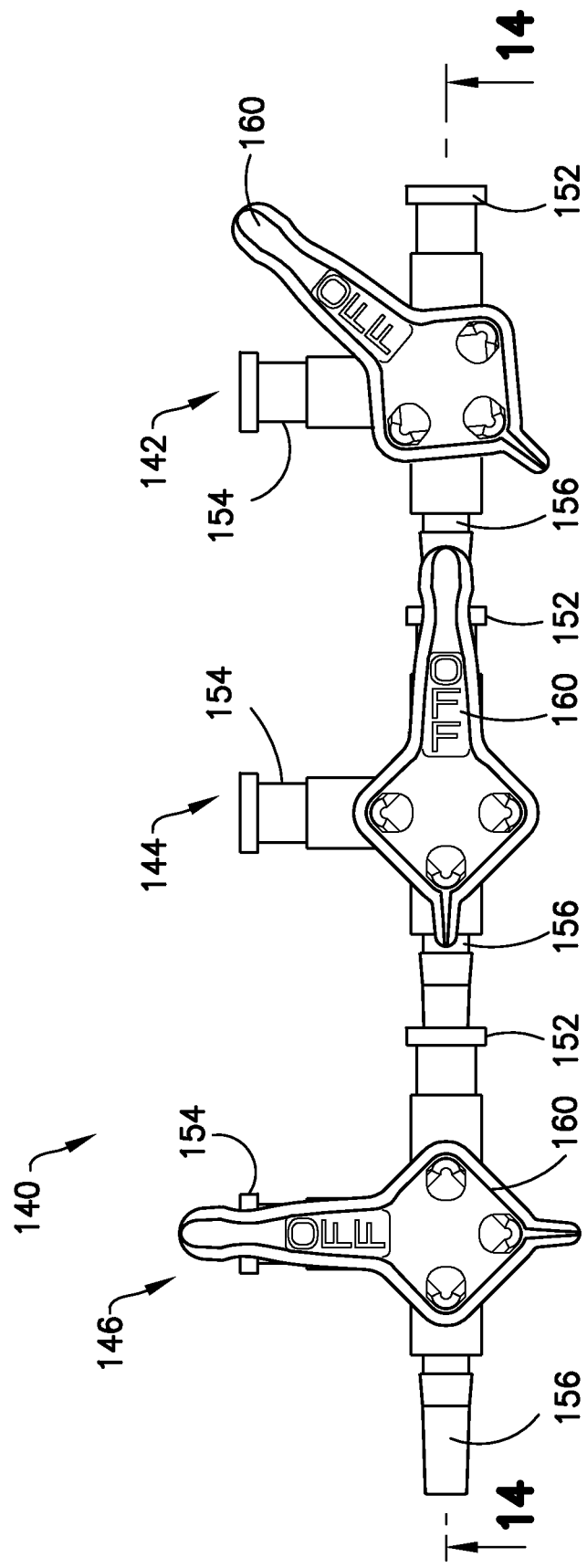
FIG. 13 is a top view showing the serially-connected fluid control valves used in the manifold shown in FIG. 4.
Figure 14:
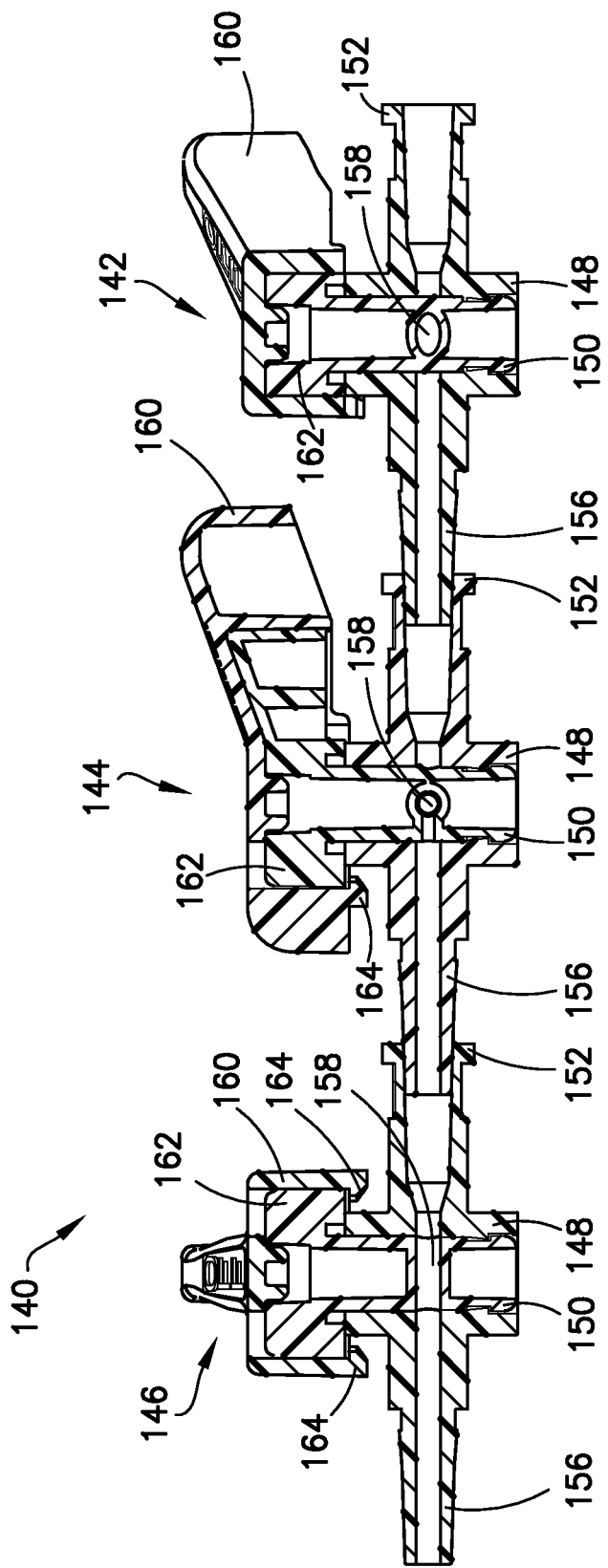
FIG. 14 is a cross-sectional view taken along lines 14-14 in FIG. 13.

Referring to FIG. 1, a fluid delivery system 10 is shown and includes a dual high and lower pressure hand manifold 100 adapted for fluid connection to a plurality of fluid sources. The fluid sources may include a low pressure, hand-operated syringe 20, a high pressure, power injector operated syringe 40, and one or more additional fluid sources or containers such as fluid source container 80 in the form of, for example, a saline bag. Referring further to FIG. 2, the hand-operated syringe 20 may be a conventional hand-operated syringe comprising a syringe barrel 22 with a discharge neck 24 having a rotational tip connector 26 at its terminal end. The rotational tip connector 26 may be, for example, a rotational luer connector. The syringe barrel 22 may be formed with opposed finger grips 28 for the user. Additionally, a plunger 30 is disposed in the syringe barrel 22. The plunger 30 may include a proximal finger grip 32 for the user.

The high pressure syringe 40 may be a syringe adapted for mechanical interface with a power injector 12, which is schematically represented in FIG. 1. A suitable high pressure syringe 40 adapted to interface with the power injector 12 may be found in United States Patent Application Publication No. 2009/0216192 to Schriver et al., incorporated herein by reference for teachings related to the high pressure syringe 40 and, further, the power injector 12. The high pressure syringe 40 generally comprises an elongated, cylindrical syringe body 42 having a front or distal end 44 and a rear or proximal end 46. The syringe body 42 generally defines an injection section 48 at the distal end 44 and an expansion section 50 at the proximal end 46. A generally cylindrical center or working section 52 of the syringe body 42 connects the injection section 48 and the expansion section 50. The center or working section 52 has a relatively uniform outer diameter. The injection section 48 tapers to form an elongated discharge neck 54, which has a relatively small inner diameter compared to the inner diameter of the center or working section 52. The injection section 48 and discharge neck 54 generally form the discharge outlet of the syringe 40. The expansion section 50 accommodates a syringe plunger (not shown). The injection section 48 is formed with a hollow alignment flange or tab 56 for orienting and aligning the syringe 40 in the power injector 12.

Additionally, the proximal end 46 of the syringe body 42 defines an outward extending radial lip 58. The radial lip 58 is adapted to engage or contact an electrical contact switch in the power injector 12 to activate the electrical switch to identify when the syringe 40 is properly loaded in the power injector 12. The radial lip 58 preferably has an outer diameter that is no greater than the outer diameter of the center or working section 52 of the syringe body 42 so that the syringe 40 may be smoothly accepted into a pressure jacket (not shown) associated with the power injector 12 during a syringe-loading procedure. A tip connector 60 is connected to the terminal end of the discharge neck 54 and a length of tubing 62, typically high pressure braided or coextruded tubing, extends from the tip connector 60 to place the high pressure syringe 40 in fluid connection with the manifold 100. Details of the tip connector 60 may be found in PCT Application No. PCT/US12/37491 filed May 11, 2012, (PCT Publication No. WO/2012/155035), incorporated herein by reference.

Referring further to remaining FIGS. 3-14, the manifold 100 includes a manifold housing 102 formed to support a plurality of fluid control valves 140 that are connected in series with one another. The manifold housing 102 is generally L-shaped and defines a longitudinal portion 104 and a lateral portion 106. The lateral portion 106 is generally orthogonal to the longitudinal portion 104. The manifold housing 102 is formed with a generally closed first side 108 and has a second side 110 that defines a recessed area or pocket 112 adapted to accept and support the fluid control valves 140. The recessed area or pocket 112 is defined by a side wall 114 that extends around the perimeter of the recessed area or pocket 112. Within the recessed area 112, the manifold housing 102 is formed with a plurality of snap-fit/friction-fit connection points or locations 116 to engage the body of the respective fluid control valves 140. Respective side openings 118 are defined in the manifold housing 102 in the area of the connection elements at locations 116. The snap-fit/friction-fit locations 116 are formed by individual flange elements 120 formed integrally with the manifold housing 102 and within the recessed area 112. The flange elements 120 secure the fluid control valves 140 in the respective snap-fit/friction-fit locations 116. Additional port openings 122 are defined in the manifold housing 102 in the area of the connection elements at locations 116 to accommodate fluid ports of the fluid control valves 140.

The lateral portion 106 of the manifold housing 102 defines a tubing retention pathway 124. The tubing retention pathway 124 defines a tubing bend of approximately 90° to allow for axial alignment between the power injector 12 and a patient. The tubing 62 extending from the tip connector 60 on the high pressure syringe 40 is positioned in the tubing retention pathway 124 and connects to a first fluid control valve of the plurality of fluid control valves 140, as described herein, to place the high pressure syringe 40 in fluid connection with the first fluid control valve 142. As further shown in FIGS. 9A-9B, the tubing pathway 124 may be provided with opposing inward-directed lips or flanges 126 such that the tubing 62 is secured in the tubing pathway 124 by a snap-fit/friction-fit connection. Further, the manifold housing 102 further comprises a stop element 128 to prevent rotation of the first fluid control valve to a position that opens a fluid path between the high pressure syringe 40 and the low pressure syringe 20 to prevent high pressure, high volume injection into the low pressure syringe 20.

The fluid control valves 140 are situated in the recessed area or pocket 112 in the manifold housing 102. The fluid control valves 140 are connected in series with one another and are desirably UV adhesively bonded together in the ganged formation shown in the Figures. The fluid control valves 140 include, in the illustrated embodiment, a first fluid control valve 142, a second fluid control valve 144, and a third fluid control valve 146. The first fluid control valve 142 is located in a first snap fit/friction-fit connection location 116 (1) adjacent the lateral portion 106 of the manifold housing 102. The second fluid control valve 144 is located in the second snap-fit/friction-fit connection location 116(2) located approximately in the middle of the manifold housing 102. The third fluid control valve 146 is located in the remaining or third snap-fit/friction-fit connection location 116(3) in the manifold housing 102 in the presently illustrated embodiment of the manifold 100. Additional or fewer fluid control valves 140 may be provided in the manifold 100, and the illustration of three (3) such fluid control valves 140 is for exemplary purposes only.

Each of the fluid control valves 140 may be in the form of a 3-position stopcock valve as illustrated, but this specific implementation of the fluid control valves 140 should not be deemed limiting. The fluid control valves 140 each comprise a cylindrical valve body 148 and a valve stem 150 disposed in the cylindrical valve body 148 to control fluid flow between a plurality of ports on the cylindrical valve body 148. The cylindrical valve body 148 comprises a first port 152, a second port 154, and a third port 156. The first and second ports 152, 154 on each cylindrical valve body 148 are typically fluid inlet ports, and the third port 156 is typically an outlet port. The valve stem 150 defines a flow passage 158 for placing one of the first or second "inlet" ports 152, 154 in fluid connection with the third port 156, or to place the first "inlet" port 152 in fluid connection with the second "inlet" port 154 in certain instances. A valve handle 160 is secured onto the valve stem 150, typically by a snap-fit/friction-fit connection. As shown, for example, in FIG. 11, the valve stem 150 has a head or end portion 162 and the valve handle 160 is provided with engaging tabs 164 for a snap-fit/friction-fit connection onto the head or end portion 162 of the valve stem 150 to secure the valve handle 160 onto the valve stem 150. The respective ports 152, 154, 156 on the cylindrical valve body 148 may be formed for conventional luer type engagements, threaded or unthreaded, with one another or with another element, such as the low pressure syringe 20, as an example.

As illustrated in the embodiment shown in FIGS. 2-14, the respective fluid control valves 142, 144, 146 are connected in series with one another and bonded together to form a singular unit. Beginning with the first fluid control valve 142, the first fluid control valve 142 has the first port 152 in fluid connection with the low pressure syringe 20 via the rotational luer connector 26 on the terminal end of the discharge neck 24 of the low pressure syringe 20. The second port 154 is in fluid connection with the high pressure syringe 40 via the tubing 62 that extends from the tip connector 60. The opposing end of the tubing 62 comprises a luer-type connector 64 or like connector to connect to the second port 154 on the cylindrical valve body 148 of the first fluid control valve 142. The first fluid control valve 142 in the present embodiment is capable of two particular flow states. In a first rotational position of the valve stem 150 in the cylindrical valve body 148 of the first fluid control valve 142, the first port 152 is in fluid connection with the third port 156 permitting fluid from the low pressure syringe 20 to pass through the first fluid control valve 142 and exit via the third port 156, or fluid may be drawn into the low pressure syringe 20 via the third port 156 should it be desired, for example, to draw fluid into the low pressure syringe 20 from the fluid source container 80. In a second rotational position of the valve stem 150 in the cylindrical valve body 148 of the first fluid control valve 142, the second port 154 is in fluid connection with the third port 156 permitting fluid from the high pressure syringe 40 to pass through the first fluid control valve 142 and exit via the third port 156, or fluid may be drawn into the high pressure syringe 40 via the third port 156 should it be desired, for example, to draw fluid into the high pressure syringe 40 from the fluid source container 80. Due to the presence of the stop element 128, the valve stem 148 may not be placed in a position that opens a fluid path between the high pressure syringe 40 and the low pressure syringe 20 to prevent high pressure, high volume injection into the low pressure syringe 20, as mentioned previously. The first fluid control valve 142 is operable as a syringe stopcock.

Next, the second fluid control valve 144 is disposed in the second snap-fit/friction-fit location 116(2) located approximately in the middle of the longitudinal portion 104 of the manifold housing 102. The second fluid control valve 144 has the first port 152 in fluid connection with the third port 156 of the first fluid control valve 142. Accordingly, fluid flow from either the first port 152 (e.g., low pressure syringe 20) or the second port 154 (e.g., high pressure syringe 40) of the first fluid control valve 142 may pass to the first port 152 of the second fluid control valve 144 depending on the rotational position of the valve stem 150 of the first fluid control valve 142. The second port 154 on the cylindrical valve body 148 of the second fluid control valve 144 is typically in fluid connection to a saline bag or another such fluid source container 80, as shown in FIG. 1. The fluid source container 80 is connected to the second port 154 of the second fluid control valve 144 by a fluid path 82 including a spike 84 to establish a fluid connection with the fluid source container 80, and branched tubing 86. The branched tubing 86 provides fluid connection between the second port 154 and the fluid container or source 80 and, further, a waste container 88. Oppositely operable check valves 90, 92 are provided in the fluid path 82 to prevent reverse flow into the fluid source container 80 and prevent gravity flow from the waste container 88 to the second port 154. Thus, fluid flow is unidirectional into the waste container 88.

As with the first fluid control valve 142, the rotational position of the valve stem 150 in the cylindrical valve body 148 controls fluid flow through the second fluid control valve 144. For example, in a first rotational position of the valve stem 150 in the cylindrical valve body 148 of the second fluid control valve 144, fluid from the first fluid control valve 142 is permitted to enter the first port 152 of the second fluid control valve 144 from the third port 156 of the first fluid control valve 142 and exit via the third port 156 of the second fluid control valve 144, while the second port 154 is blocked. In this rotational position, fluid from either the low pressure syringe 20 or the high pressure syringe 40 may reach the third port 156 of the second fluid control valve 142 depending on the rotation position of the valve stem 150 of the first fluid control valve 142.

In a second rotational position of the valve stem 150 in the cylindrical valve body 148 of the second fluid control valve 144, fluid is permitted to enter into and exit from the second fluid control valve 144 via the second port 154 and pass to the first port 152 through flow passage 158. In this rotational position, fluid may enter or exit via the second port 154. In this second rotational position, the third port 156 is blocked and fluid from the fluid source container 80 is accessible to the low or high pressure syringes 20, 40 depending on the rotational position of the valve stem 150 in the cylindrical valve body 148 of the first fluid control valve 142. Alternatively, in this second rotational position, fluid from the low or high pressure syringes 20, 40 may be expelled into the waste container 88 depending on the rotational position of the valve stem 150 in the cylindrical valve body 148 of the first fluid control valve 142.

In a third rotational position of the valve stem 150 in the cylindrical valve body 148 of the second fluid control valve 144, the second port 154 is in fluid connection with the third port 156 via flow passage 158, thereby isolating both the low and high pressure syringes 20, 40 from any downstream elements. This last rotational position enables a flow of fluid from the fluid source container 80 to reach downstream elements, namely the third fluid control valve 146, under gravity flow, if so desired. The second fluid control valve 144 is operable as a saline stopcock.

Further, the third fluid control valve 146 is disposed in the third snap-fit/friction-fit location 116(3) located approximately at the end of the longitudinal portion 104 of the manifold housing 102. The third fluid control valve 146 has the first port 152 in fluid connection with the third port 156 of the second fluid control valve 144. Accordingly, fluid flow from either the first port 152 or the second port 154 of the first fluid control valve 142 may pass to the first port 152 of the third fluid control valve 144 depending on the rotational positions of the valve stems 150 of the first and second fluid control valves 142, 144. The second port 154 on the cylindrical valve body 148 of the third fluid control valve 146 is typically connected to a hemodynamic pressure transducer 14, as shown in FIG. 1. Further, the third port 156 on the cylindrical valve body 148 of the third fluid control valve 146 may be connected to a patient connector fluid path set 16 having a tubing stabilizer 18, as also shown in FIG. 1.

As with the first and second fluid control valves 142, 144, the rotational position of the valve stem 150 in the cylindrical valve body 148 controls fluid flow through the third fluid control valve 146. For example, in a first rotational position of the valve stem 150 in the cylindrical valve body 148 of the third fluid control valve 146, fluid from the second fluid control valve 144 is permitted to enter the first port 152 of the third fluid control valve 146 from the third port 156 of the second fluid control valve 144 and exit via the third port 156 of the third fluid control valve 146, while the second port 154 is blocked. In this rotational position, fluid flow from the low and high pressure syringes 20, 40 may pass through the third fluid control valve 146 to reach the patient connector fluid path set 16 depending on the rotational positions of the valve stem 150 of the first and second fluid control valves 142, 144. Alternatively, in this rotational position, fluid from the fluid source container 80 may pass through the third fluid control valve 146 to reach the patient connector fluid path set 16 under gravity flow, depending on the rotational position of the valve stem 150 of the second fluid control valve 144.

In a second rotational position of the valve stem 150 in the cylindrical valve body 148 of the third fluid control valve 146, the hemodynamic pressure transducer 14 is in fluid connection with the patient connector fluid path set 16 connected to the third port 156 of the third fluid control valve 146 to permit blood pressure waveform readings to be measured by the hemodynamic pressure transducer 14. In this rotational position, fluid flow from the upstream low and high pressure syringes 20, 40 is blocked from entering the first port 152 of the third fluid control valve 146, as is fluid from the fluid source container 80. In a third rotational position of the valve stem 150 in the cylindrical valve body 148 of the third fluid control valve 146, the second port 154 is in fluid connection with the first port 152, thereby entirely isolating the patient connector fluid path set 16 from upstream components. The third fluid control valve 146 is operable as a hemodynamic pressure reading stopcock.

While the foregoing discussion of the first, second, and third fluid control valves 142, 144, 146 provides operational details of the first, second, and third fluid control valves 142, 144, 146, the foregoing discussion is not intended to list each and every permutation of the operational valve states for the first, second, and third fluid control valves 142, 144, 146. One skilled in the valve art would readily be able to identify the entire range of permutations for the operational valve states for the first, second, and third fluid control valves 142, 144, 146. Thus, the foregoing discussion should not be deemed as limiting or exhaustive of the possible permutations of the operational valve states for the first, second, and third fluid control valves 142, 144, 146.

To prime the fluid delivery system 10 with fluid, the following exemplary procedure may be followed. The second fluid control valve 144 may be placed in a state to permit fluid communication between the first port 152 and the second port 154, and the first fluid control valve 142 may be placed in a state to permit fluid communication between the first port 152 and the third port 156. The fluid path between the fluid source container 80 and the low pressure syringe 20 may be filled with fluid and purged of air. During this step, the low pressure syringe 20 is filled with fluid from the fluid source container 80, typically saline. Next, the second fluid control valve 144 may be placed in a state to permit fluid communication between the first port 152 and the third port 156, and the third fluid control valve 146 may be placed in a state to permit fluid communication between the first port 152 and the second port 154. The low pressure syringe 20 may then be used to prime the hemodynamic pressure transducer 14 with fluid and purge air. Next, the second fluid control valve 144 may be placed in a state to permit fluid communication between the first port 152 and the third port 156, the third fluid control valve 146 may be placed in a state to permit fluid communication between the first port 152 and the third port 156, and the first fluid control valve 142 is placed in a state to permit fluid communication between the second port 154 and the third port 156. The fluid path from the high pressure syringe 40 (for example, a prefilled syringe or a fill syringed by a user or operator) to the second port 154 of the first fluid control valve 142 may be filled with fluid and purged of air. Alternatively, the high pressure syringe 40 may be primed with fluid following the general priming procedure outlined above in connection with the low pressure syringe 20, with appropriate positional settings of the second fluid control valve 144 to permit fluid from the fluid source container 80 to reach the high pressure syringe 40.

After the foregoing procedures have been completed, a patient catheter may be connected to the patient connector fluid path set 16. The second and third fluid control valves 144, 146 may each be placed in a state to permit fluid communication between the first port 152 and the third port 156, and the first fluid control valve 142 may be placed in a state to permit fluid communication between the first port 152 and the third port 156. The plunger 30 of the low pressure syringe 20 may be drawn back until blood and any air are drawn into the syringe barrel 22. The second fluid control valve 144 is then placed in a state to permit fluid communication between the first port 152 and the second port 154 and the contents (e.g., air, saline, and blood) of the low pressure syringe 20 may be emptied into the waste container 88, and the low pressure syringe 20 may be refilled with fluid from the fluid source container 80. The immediately foregoing steps may be repeated until air has been removed the patient catheter.

The fluid delivery system 10 as described in the foregoing has typical uses in cardiology imaging procedures. The fluid delivery system 10 may be used in these imaging procedures and may be used, for example, to: (1) take hemodynamic blood pressure readings; (2) perform saline flushing of a patient catheter connected to the patient connector fluid path set 16; (3) support imaging of the coronaries with low pressure and low volume contrast injections from the low pressure syringe 20; and (4) support imaging of large arteries with high pressure (e.g., between 1000-1200 psi) and high volume contrast injections from the high pressure syringe 40.

The fluid delivery system 10 and the hand-operated manifold 100 are capable of delivering high volume and high pressure injections, typically contrast, utilizing the high pressure power injector syringe 40, and low volume and low pressure injections, typically saline, utilizing the low pressure syringe 20. Typical low pressure hand manifold systems utilize a single hand syringe that can deliver low volume and low pressure injections of saline or contrast for imaging of the coronary arteries. In these known systems, the low pressure hand manifold must be disconnected from a patient catheter and a power injector must be connected to the patient catheter to perform a high pressure, high volume injection for imaging of the larger coronary arteries or chambers of the heart. Additionally, as a result of having to connect the power injector to the patient catheter, the patient's hemodynamic blood pressures are not available until the low pressure hand manifold is reattached to the patient catheter. In the present fluid delivery system, the manifold 100 does not need to be disconnected to obtain hemodynamic blood pressure readings as the hemodynamic fluid control valve 146 permits these readings to be obtained at all times. These readings may be taken at any time by placing the third fluid control valve 146 in a state to permit fluid communication between the second port 154 and the third port 156 of the third fluid control valve 146. Moreover, as the fluid delivery system 10 has both low and high pressure syringes 20, 40 available at all times, the manifold 100 is automatically configurable to perform low and high pressure injections and nothing needs to be disconnected/reconnected as is the case in known low pressure hand manifolds currently found in the medical field. This saves procedure time and is less likely to cause associated problems with disconnection and reconnection and subsequent re-purging of air from the system.

Moreover, multi-port hand manifolds known in the medical field are typically injection molded and, as a result of the injection molding process, it is often difficult to maintain acceptable tolerances on the press-fits between the manifold ports and stopcock handles. The amount of press-fit controls the pressure rating and the stopcock torque to rotate the handle. Current polymer materials available are not able to withstand the high-force press fits without causing the polymer to yield and creep-rupture over time causing leaks. The torque required to move the stopcock handle is also controlled by the press-fit and it is desirable for the handle to be easy to turn. The tolerances associated with these known multi-port hand manifold designs are controlled precisely to "tune in" the press-fit to achieve a desired pressure rating and control torque. This tight tolerance scenario is exacerbated by the presence of multiple ports; the more ports, the more difficult it is to control the tolerances on each port. In contrast, in the present manifold 100, the fluid control valves 140 are bonded together in series with one another using UV adhesive bonding which enables the "ganged" fluid control valves 140 in the manifold 100 to withstand high pressures (e.g., 1000-1200 psi) and overcome the foregoing deficiencies known with known multi-port hand manifolds.

The fluid delivery system 10 and manifold 100 makes injection of viscous contrast into small blood vessels using small bore catheters significantly easier because the power injector 12 can easily develop the force needed to push the contrast through the small catheters and into small arteries to opacify the small arteries. Known hand manifolds using a hand syringe cannot develop the force needed to accomplish the foregoing result. Additionally, the use of a power injector 12 in the fluid delivery system 10 improves image reproducibility because the power injector 12 is computer-controlled versus manually-controlled in the case of known hand manifolds using a hand syringe alone.

While embodiments of a fluid delivery system including a fluid path set comprising a manifold with a plurality of fluid control valves and operational characteristics of the fluid delivery system and fluid path set were discussed in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A fluid path set for a fluid delivery system, comprising:
a manifold comprising a plurality of fluid control valves in series fluid communication, wherein a first fluid control valve comprises a first port, a second port, and a third port, wherein the third port of the first fluid control valve is in fluid connection with a first port of a second fluid control valve;
a low pressure hand-operated syringe in fluid connection with the first port of the first fluid control valve; and
a high pressure syringe configured for operation by a power injector and in fluid connection with the second port of the first fluid control valve,
wherein the plurality of fluid control valves and the high pressure syringe can withstand pressures of 1000-1200 psi.

2. The fluid path set of claim 1, wherein the plurality of fluid control valves each comprise a multi-position stopcock valve.

3. The fluid path set of claim 1, wherein the manifold further comprises a manifold housing, and the plurality of fluid control valves are in friction-fit connection within the manifold housing.

4. The fluid path set of claim 1, wherein the manifold comprises an L-shaped manifold housing comprising a longitudinal portion and a lateral portion, and wherein the second port of the first fluid control valve is generally coaxial with the lateral portion.

5. The fluid path set of claim 4, wherein the lateral portion defines a tubing retention pathway to accommodate tubing connecting the high pressure syringe with the second port of the first fluid control valve.

6. The fluid path set of claim 5, wherein the tubing retention pathway defines a tubing bend of approximately 90°.

7. The fluid path set of claim 1, wherein the manifold further comprises a manifold housing, the manifold housing comprising a stop element to prevent rotation of the first fluid control valve to a position that opens a fluid path between the high pressure syringe and the low pressure hand-operated syringe.

8. A fluid delivery system, comprising:
a power injector including a high pressure syringe operated by the power injector;
a manifold comprising a plurality of fluid control valves in series fluid communication, wherein a first fluid control valve comprises a first port, a second port, and a third port, wherein the third port of the first fluid control valve is in fluid connection with a first port of a second fluid control valve; and
a low pressure hand-operated syringe in fluid connection with the first port of the first fluid control valve,
wherein the high pressure syringe is in fluid connection with the second port of the first fluid control valve; and
wherein the plurality of fluid control valves and the high pressure syringe can withstand pressures of 1000-1200 psi.

9. The fluid delivery system of claim 8, wherein the plurality of fluid control valves each comprise a multi-position stopcock valve.

10. The fluid delivery system of claim 8, wherein the manifold further comprises a manifold housing, and the plurality of fluid control valves are in friction-fit connection within the manifold housing.

11. The fluid delivery system of claim 8, wherein the manifold housing comprises an L-shaped manifold comprising a longitudinal portion and a lateral portion, and wherein the second port of the first fluid control valve is generally coaxial with the lateral portion.

12. The fluid delivery system of claim 11, wherein the lateral portion defines a tubing retention pathway to accommodate tubing connecting the high pressure syringe with the second port of the first fluid control valve.

13. The fluid delivery system of claim 12, wherein the tubing retention pathway defines a tubing bend of approximately 90°.

14. The fluid delivery system of claim 8, wherein the manifold further comprises a manifold housing, the manifold housing comprising a stop element to prevent rotation of the first fluid control valve to a position that opens a fluid path between the high pressure syringe and the low pressure hand-operated syringe.

15. A fluid path set for a fluid delivery system, comprising:
a manifold comprising a plurality of fluid control valves in series fluid communication, each of the plurality of fluid control valves comprising a first port, a second port, and a third port, wherein the third port of a first fluid control valve of the plurality of fluid control valves is in fluid connection with the first port of a second fluid control valve of the plurality of fluid control valves, and the third port of the second fluid control valve is in fluid connection with the first port of a third fluid control valve of the plurality of fluid control valves;
a low pressure hand-operated syringe in fluid connection with the first port of the first fluid control valve; and
a high pressure syringe configured for operation by a power injector and in fluid connection with the second port of the first fluid control valve,
wherein the plurality of fluid control valves and the high pressure syringe can withstand pressures of 1000-1200 psi.

16. The fluid path set of claim 15, further comprising a hemodynamic pressure transducer in fluid connection with the second port of the third fluid control valve.

17. The fluid path set of claim 15, wherein the plurality of fluid control valves each comprise a multi-position stopcock valve.

18. The fluid path set of claim 15, wherein the manifold further comprises a manifold housing, and the plurality of fluid control valves are in friction-fit connection within the manifold housing.

19. The fluid path set of claim 15, wherein the manifold comprises an L-shaped manifold housing comprising a longitudinal portion and a lateral portion, and wherein the second port of the first fluid control valve is generally coaxial with the lateral portion.

20. The fluid path set of claim 19, wherein the lateral portion defines a tubing retention pathway to accommodate tubing connecting the high pressure syringe with the second port of the first fluid control valve.

21. The fluid path set of claim 20, wherein the tubing retention pathway defines a tubing bend of approximately 90°.

22. The fluid path set of claim 15, wherein the manifold further comprises a manifold housing, the manifold housing comprising a stop element to prevent rotation of the first fluid control valve to a position that opens a fluid path between the high pressure syringe and the low pressure hand-operated syringe.

* * * * *

UNITED STATES PATENT AND TRADEMARK OFFICE
CERTIFICATE OF CORRECTION

PATENT NO. : 9,259,527 B2
APPLICATION NO. : 13/755883
DATED : February 16, 2016
INVENTOR(S) : Spohn et al.

Page 1 of 1

It is certified that error appears in the above-identified patent and that said Letters Patent is hereby corrected as shown below:

On Title Page 2, item 56, under "OTHER PUBLICATIONS", in Column 2, Line 1, delete "Blook" and insert -- Blood --, therefor.

IN THE SPECIFICATION:
In Column 8, Lines 29-30, delete "third fluid control valve 144" and insert -- second fluid control valve 144 --, therefor.

Signed and Sealed this
Tenth Day of May, 2016

Michelle K. Lee
*Director of the United States Patent and Trademark Office*